United States Patent [19]

Eisenbrand et al.

[11] Patent Number: 4,615,835
[45] Date of Patent: Oct. 7, 1986

[54] STEROID ESTERS OF N-(2-HALOGENETHYL)-N-NITROSO-CARBAMOYLAMINO AND ACIDS AND PEPTIDES THEREFORE, AS WELL AS METHOD FOR PREPARING THEM

[75] Inventors: Gerhard Eisenbrand, Sandhausen; Joachim Schreiber, Stelzenberg, both of Fed. Rep. of Germany

[73] Assignee: Stiftung Deutsches Krebsforschungs Zentrum, Heidelberg, Fed. Rep. of Germany

[21] Appl. No.: 731,861

[22] Filed: May 8, 1985

Related U.S. Application Data

[63] Continuation-in-part of Ser. No. 557,138, Nov. 17, 1983.

[51] Int. Cl.[4] .................................................. C07J 1/00
[52] U.S. Cl. .................................................. 260/397.5
[58] Field of Search ................. 424/177; 260/397.5, 260/112.5

[56] References Cited

U.S. PATENT DOCUMENTS 4,177,269 12/1979 Fex et al. ................. 260/239.5
4,181,669 1/1980 Hansen et al. ............... 260/397.4

*Primary Examiner*—Elbert L. Roberts
*Attorney, Agent, or Firm*—Browdy and Neimark

[57] ABSTRACT

Steroid-N-(2-halogen ethyl)-N-nitroso-carbamoylamino acid or peptide esters of the general formula:

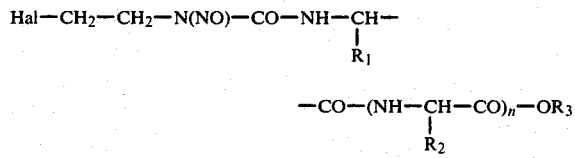

where $R_1$ and $R_2$, which may be identical or different, mean the radical of an amino acid beyond the C atom in the beta position (if present), $R_3$ means the radical of a steroid or a stilbene derivative pharmacologically similar in action, n is a number from 0-5 and Hal stands for chlorine or fluorine, as well as the method for preparing them by the conversion of an appropriate carbamoyl-amino acid or carbamoyl-peptide in a manner known per se with steroid alcohols or the conversion of steroid-amino acid or steroid-peptide esters with corresponding N-nitroso-carbamoylation or corresponding N-nitroso-carbamoyl-amino acids or peptides in a manner known per se.

1 Claim, No Drawings

STEROID ESTERS OF N-(2-HALOGENETHYL)-N-NITROSO-CARBAMOYLAMINO AND ACIDS AND PEPTIDES THEREFORE, AS WELL AS METHOD FOR PREPARING THEM

This is a continuation-in-part of parent, co-pending application Ser. No. 557,138, filed Nov. 17, 1983, the entire contents of which are hereby incorporated by reference.

FIELD OF INVENTION

The present invention relates to antineoplastic chemotherapeutic agents and, more particularly, to certain therapeutic 2-halogen-alkylnitrosourea derivatives.

BACKGROUND

N-(2-ethyl chloride)-N-nitrosoureas ("CNU"), such as 1,3-bis-(2-ethyl chloride)-1-nitrosourea (BCNU), 1-(2-ethyl chloride)-3-cyclohexyl-1-nitrosourea (CCNU) and 1-(2-ethyl chloride)3-(4-methyl) cyclohexyl-1-nitrosourea (MeCCNU) are important antineoplastic chemotherapeutic agents, from the clinical standpoint as well. (*Nitroso-ureas in Cancer treatment,* B. Serrou, P. S. Schein and J.-L. Imbach, editors, Elsevier/North-Holland Biomedicals Press, 1981; *Nitrosoureas: current status and new developments,* Academic Press, New York, 1981).

Along with their therapeutic efficacy, however, these substances also have a long-lasting cumulative toxicity (Eisenbrand et al., in: *Nitrosoureas in Cancer Treatment,* Elsevier 1981).

In order to obtain substances having a better therapeutic index, nitrosoureas have lately been synthesized with various substitutions (for instance, sugar, peptides, DNA bases) and experimentally tested.

It has been found that a series of tumors contain hormone receptors or are hormone-dependent. The attempt has already been made several times to improve the chemotherapy of such tumors by chemically bonding alkylanes, for example, to hormones in order to exploit the receptor affinity of the hormones for attaining target-specific transporting of the cytostatic alkylane into the tumor tissue. Some examples of substances of this type are Prednimustin ®, an ester of prednisolone and the alkylane chlorambucil (a phenyl-butyric acid-mechlorethamine hydrochloride derivative), or Estracyt ®, an N,N-bis (2-ethyl chloride)-3-carbamate of the estradiol-17-$\beta$-phosphate. (*Cancer Chemotherapy,* edited by H. M. Pinedo, Excerpta Medica, Amsterdam-Oxford, 1979 and 1980.)

DESCRIPTION OF INVENTION

In contrast to the directly alkylating mechlorethamine hydrochloride derivatives of the prior art, the present case relates to 2-halogen-alkylnitrosourea derivatives, which release a cross-linking alkylane only upon their decomposition in vivo. The CNU grouping must therefore be evaluated differently in both chemical and biological terms from the mechlorethamine hydrochloride group. As a rule, the CNU derivatives have a wider therapeutic range than the mechlorethamine hydrochloride derivatives.

The present compounds are steroid-N-(2-halogenethyl)-N-nitroso-carbamoyl-amino acid or peptide esters of the general formula:

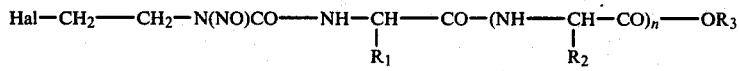

wherein $R_1$ and $R_2$, which may be identical or different, signify the radical of an amino acid beyond the carbon atom in the beta position (if present), $R_3$ signifies the radical of a steroid or of a pharmacologically similarly effective stilbene derivative, n is a number from 0-5 and Hal signifies chlorine or fluorine.

In the present compounds a steroid molecule or a stilbene derivative acting pharmacologically similarly is bonded via an ester bond with an N-(2-halogen ethyl)-N-nitroso-carbamoylamino acid or with a peptide chain, the terminal amino acids of which carry the N-(2-halogen ethyl)-N-nitroso-carbamoyl group. The term "steroid" here also encompasses pharmacologically similarly acting stilbene derivatives having at least one OH group without steric hindrance. The steroids are preferably of the estrane, androstane or pregnane series, or corticosteroids. In the formula above, $R_3$ is thus a steroid preferably as follows:

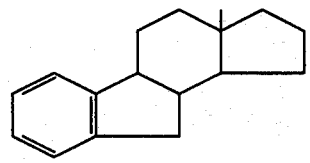

Estrane

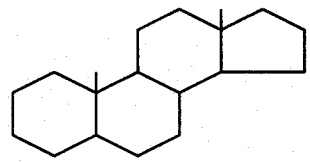

Androstane

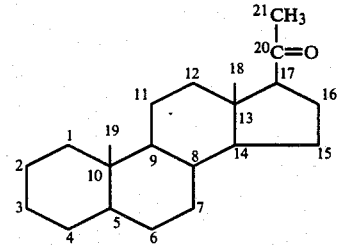

Pregnane

The OH groups used for the purpose of esterification are preferably located in positions 3, 6, 7, 15, 16, 17 and 21 of the pregnane structure. Additionally present OH groups may be free or else etherified (for instance, with methyl or ethyl) or esterified (for instance, with acetate or propenate or $OCOC_6H_5$).

The stilbene derivatives ($R_3$ in the formula above) are preferably those having the following structures:

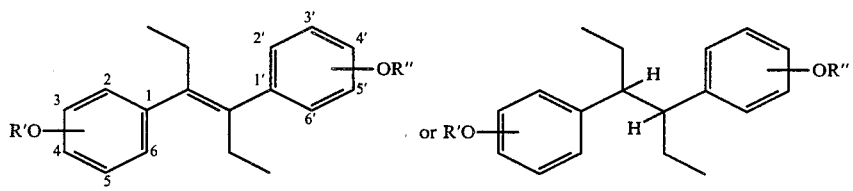

with R' = Hal—CH$_2$—CH$_2$—N(NO)—CO—NH—CH(R$_1$)—CO—(NH—CH(R$_2$)—CO)$_n$—.

R' is accordingly the radical for supplementing the ethyl chloride nitrosourea with R$_1$ and R$_2$ retaining their meaning given above; that is, they are radicals of amino acids. R''=H or R' or a low alkyl, in particular methyl or ethyl, or acyl, in particular acetyl or benzoyl. The OR' or OR'' substitutions are located at identical or different positions on the benzene rings, in particular in positions, 3,3'; 4,4' and 3,4'. The ethylene double bond of the stilbene body may also be hydrogenated, as is evident from the formulas above.

To prepare these compounds, a CNU amino acid, a CNU di-, tri- or oligopeptide (up to hexapeptide), synthesized in accordance with W. Tang, G. Eisenbrand, *Arch. Pharm.* 413, 910–917 (1981) and with German Patent Application No. P 31 34 923.4, is put into an activated form, such as the imidazolide or a mixed acid anhydride (such as paratoluolsulfonic acid) and converted with a steroid alcohol, which carries at least one OH group without steric hindrance (for instance, the hindered 11—OH group not react). The CNU acid component can also be esterifid directly with the steriod alcohol, using condensation agents such as dicyclohexylcarbodiimide. These reactions can be performed either with or without acylation catalysts such as 4-dimethylaminopyridine. If several OH groups are contained in the steriod, then the most reactive of them preferably react. This type of compound can also be prepared by beginning with a steroid amino acid ester and appending to it the CNU function, for instance by means of conversion with N-(2-ethyl chloride) N-nitroso-carbamoyl azide. Finally, this steroid amino acid ester can also be converted into the desired product with CNU amino acids or CNU di-, tri- or oligopeptides (up to pentapeptides) with the acid of mild condensation reagents such as dicyclohexylcarbodiimide.

The reactions can be illustrated as follows:

A. Hal—CH$_2$—CH$_2$—N(NO)CO—NH—CHR$_1$—CO—(NH—CHR$_2$—CO)$_n$—OH

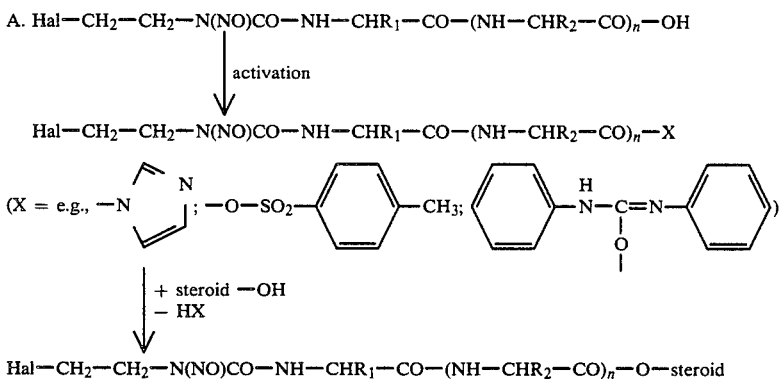

R$_1$, R$_2$, n and Hal have the same meanings here and in models B and C as in claim 1. X is a reactive monovalent group.

B. Steroid-O—(CO—CHR$_2$—NH)$_n$—CO—CHR$_1$—NH$_2$ + X—CO—N(NO)—CH$_2$—CH$_2$—Hal

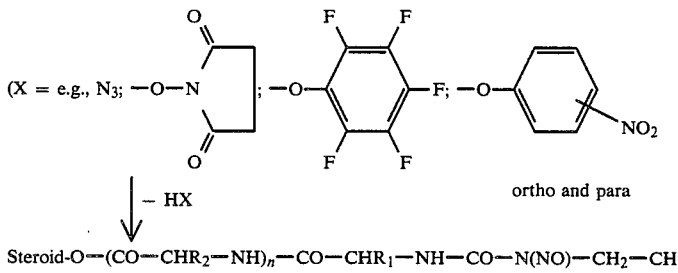

Steroid-O—(CO—CHR$_2$—NH)$_n$—CO—CHR$_1$—NH—CO—N(NO)—CH$_2$—CH$_2$—Hal

C. Steroid-O—(CO—CHR$_2$—NH)$_k$—CO—CHR$_2$—NH$_2$ +

-continued

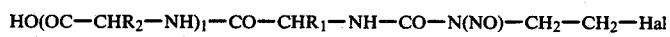

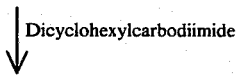

with
k=0–3
l=0–4
n=0–5.

The radicals $R_1$ and $R_2$ are radicals of amino acids beyond the carbon atom in the beta position. In the case of aminoacetic acid, this carbon atom is missing, so that these radicals then mean hydrogen. The following can be named as further radicals:

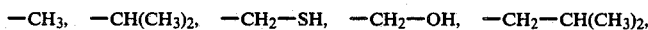

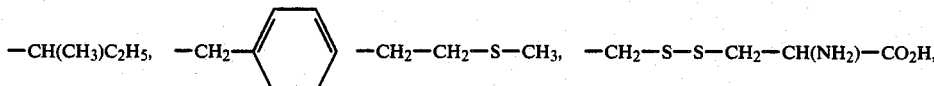

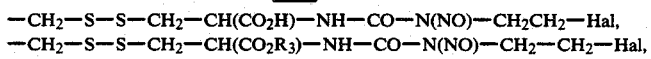

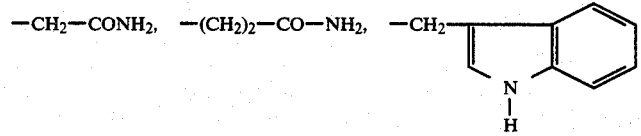

$R_1$ and $R_2$ may be the same or different; if n>1, the radicals $R_2$ may also be identical or different among each other.

$R_3$ stands for the radical of a steroid, in particular steroids which can be assigned to the classes of the androgens, estrogens, gestagens and corticosteroids; however, it can also stand for the radical of a stilbene derivative having a pharmacologically similar action, such as diethylstilbestrol.

The symbol Hal here stands for fluorine or chlorine.

In the variant method B, the reactive group X may be, in particular, $N_3$, $O-C_6F_5$,

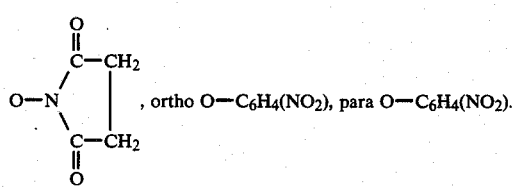

, ortho $O-C_6H_4(NO_2)$, para $O-C_6H_4(NO_2)$.

In the method variant, dicyclohexylcarbodiimide is preferred as the condensation agent. The alternative possibility also exists here of performing a conversion in the aqueous system, using water-soluble carbodiimides, such as 1-cyclohexyl-3-(2-morpholino-ethyl)-carbodiimide-metho-4-toluolsulfonate or 1-ethyl-3-(3-dimethylaminopropyl)-carbodiimide hydrochloride. In the case of water-soluble carbodiimides, it is thus also possible to use aqueous solvent systems.

The present compounds have relatively low toxicity and are useful as antineoplastic chemotherapeutic agents as indicated in more detail in said patent application, the entire contents of which are incorporated by reference.

The following Examples illustrate the invention:

EXAMPLE 1

Preparation of the 17-ester is effect in two steps.

(a) N-(2-chloroethyl)-N-nitroso carbamoyl-L-alanyl-L-alanine-estradiol-17-ester:

In a 100 ml three-necked bottle equipped with thermometer, drying tube and magnetic stirrer, 1.8 g (11 mmol) of N,N-carbonyldiimadazole are added to 50 ml absolute tetrahydrofuran (THF). While stirring 2.95 g (10 mmol) of N-(2-chloroethyl)-N-nitroso-carbamoyl-L-alanyl-L-alanin are added in portions. During this time the bottle is evacuated a few times using a water jet vacuum. Then stirring is continued for half an hour at room temperature and then 2.4 g (6.7 mmol) of estradiol-3-tetrahydropyranyl-ether are added. After 20 hours the THF is removed in a rotary evaporator and the residue is dissolved in a mixture of dichloromethane/THF=100/1 and filtered over silica gel. Purification is carried out by chromatography on a lobar (low pressure) column (filled with Merck silica gel) with dichloromethane/3% THF.

Then the resultant substance is recrystallized from dichloromethane/n-hexane.

(b) This substance, N-(2-chloroethyl)-N-nitrosocarbamoyl-L-alanyl-L-alanin-estradiol-17-ester-3-tetrahydropyranyl-ether, is dissolved in 50 ml tetrahydrofuran. To this solution a little p-toluene sulphonic acid is added and the mixture is stirred for 14 hours at room temperature. Then the solution is evaporated in a rotary evaporator and the residue is dissolved in dichloromethane and chromatographed on silica gel with dichloromethane until all unreacted starting material is separated. By elution with dichloromethane/tetrahydrofuran20/1 there is obtained a pure product which is recrystallized from dichloromethane/n-hexane.

Yield: 50% of theory, light yellow needles, melting point: 118° C. (dec.)

Elementary analysis, Ir and $^1$H-NMR-Spectra confirm the structure of the product.

EXAMPLE 2

(a) N-(2-chloroethyl)-N-nitrosocarbamoyl-L-alanyl-estradiol-17-ester-3-tetrahydropyranyl-ether:

The preparation is effected as shown in Example 1 by reacting 1.8 g of N,N-carbonyldiimidazole with 2.3 g (10 mmol) of N-(2-chloroethyl)-N-nitroso-carbamoyl-L-alanine and 2.4 g (6.7 mmol) estradiol-3-tetrahydropyranyl-ether. Chromatography on the lobar (low pressure) column is carried out with dichloromethane/1.5% THF.

Yield 2.55 g=68% of theory, light yellow needles, melting point 125° C. (decomposition).

(b) This compound is dissolved in THF, added with a small amount of p-toluene sulphonic acid as shown in Example 1 and stirred for 10 to 20 hours at room temperature and chromatographed on silica gel (dichloromethane/THF=50/1) which results in N-(2-chloroethyl)-N-nitrosocarbamoyl-L-alanyl-estradiol-17-ester.

Yield 85% of theory, light yellow needles (from dichloromethane/petrolether), melting point 143° C. (decomposition).

Elementary analysis, $^1$HNMR and $^{13}$C NMR as well as UV and IR-spectra confirm the structure of the product.

EXAMPLE 3

N-(2-chloroethyl)-N-nitrosocarbamoyl-L-alanine-estradiol-3,17-diester (CNC-L-alanine-estradiol-3,17-diester): Mp. 65° C. (dec.) light yellow crystals from aceton/hexane (with an excess of activated CNC-L-alanine, both hydroxy-groups of estradiol were esterified).

EXAMPLE 4

Tests on rats showed remarkable differences in biological activity with regard to the site of binding to the carrier. The 17-position of estradiol is superior to the other positions tested for linking CNC-L-alanine. Esterification in position 17 not only brings about highest antitumor effectiveness, but also reduced toxicity. Already at 54 umol/kg the optimal effect of CNC-L-alanine-estradiol-17-ester is reached. This tumour inhibitory effect meets NCI criteria for high activity. This therapeutic effect which extends over two dose levels (54 and 75 umol/kg) is neither reached by unlinked nitrosoureas nor by the unlinked equimolar mixture of CNC-L-alanine and estradiol (p= 0.01). At the 54 umol/kg dose level, the unlinked mixture and the 17-linked derivative display comparably low toxicities. At the following dose, however, the linked compound retains its low toxicity and high therapeutic efficacy, whereas the unlinked mixtures becomes highly toxic and barely active.

In accordance with the concept that the 3—OH group is important for estradiol receptor binding it is not surprising that the 3-derivative is less active than its 17-congener (p<0.003). This also holds true for the corresponding 3-dipeptide derivative, which is rather similar in biological activity to CNC-L-alanine-estradiol-3-ester. The 3-derivatives are distinctly more toxic than their 17-congener. This can perhaps be attributed, at least in part, to the blocking of the 3—OH group, which is not available for detoxifying conjugation reactions.

The relevance of position 3 for toxicity is, however, not supported by the results obtained with the derivative of 6—OH-estradiol. This analogue has been designed and prepared to obtain a derivative having free OH groups in positions 3 and 17, which generally are supposed to be relevant for high receptor binding affinity. A similar rationale has recently been followed by other authors (30), who synthesized an N-Lost adduct in position 6 of estradiol. Unfortunately these authors did not give any data on receptor binding affinity or antineoplastic efficacy of this compound. We found quite unexpectedly that the CNC-L-alanine-6-hydroxyestradiol-6-ester not only was highly toxic but also completely inactive. Moreover, this compound has very low binding affinity to the cytosolic estrogen receptor (0.28% RBA). The 3,17-diester also is more toxic than the 17-monoester and displays inferior antineoplastic activity.

The results are summarized in Tables 1 to 4.

TABLE 1

Treatment of MNU—induced rat mammary carcinoma with N—(2-chloroethyl)-N—nitrosocarbamoyl (CNC)—L-alanine- and CNC—L-alanyl-L-alanine-linked to estradiol in comparison with unlinked single agents and ovariectomy

Compounds and scheme of treatment

| Structures | Treatment group | Group No.[a] | Single dose[b] | Median total dose (range) (μmol/kg) |
|---|---|---|---|---|
| Cl—(CH$_2$)$_2$—N—C—NH—CH—COOH (ON, O, CH$_3$) | CNC—L-alanine | I | a* <br> b* <br> c* | 45 <br> 67 <br> 101 | 180 (180–180) <br> 268 (67–268) <br> 202 (101–404) |
| Cl—(CH$_2$)$_2$—N—C—NH—CH—C—NH—CH—COOH (ON, O, CH$_3$, O, CH$_3$) | CNC—L-alanyl-L-alanine | II | a*** <br> b*** <br> v**** | 45 <br> 67 <br> 101 | 180 (180–180) <br> 268 (134–268) <br> 404 (202–404) |
| Cl—(CH$_2$)$_2$—N—C—NH—CH—C—O— [estradiol structure with OH] | CNC—L-alanine-estradiol-3-ester | III | a* <br> b* <br> c* | 75 <br> 105 <br> 147 | 300 (150–300) <br> 420 (105–420) <br> 441 (147–588) |
| [estradiol-6-ester structure with O—C—CH—NH—C—N—(CH$_2$)$_2$—Cl, OH] | CNC—L-alanine-6-hydroxy-estradiol-6-ester | IV | a*** <br> b*** | 38 <br> 75 | 152 (152–152) <br> 300 (150–300) |
| [estradiol-17-ester structure with O—C—CH—NH—C—N—(CH$_2$)$_2$—Cl, HO] | CNC—L-alanine-estradiol-17-ester | V | a** <br> b** <br> c* <br> d* <br> e* <br> f* | 38 <br> 54 <br> 75 <br> 105 <br> 147 <br> 206 | 152 (152–152) <br> 212 (212–212) <br> 300 (300–300) <br> 420 (420–420) <br> 588 (441–588) <br> 824 (412–824) |

TABLE 1-continued

Treatment of MNU—induced rat mammary carcinoma with N—(2-chloroethyl)-N—nitrosocarbamoyl (CNC)—L-alanine- and CNC—L-alanyl-L-alanine-linked to estradiol in comparison with unlinked single agents and ovariectomy
Compounds and scheme of treatment

| Structures | Treatment group | Group No.[a] | Single dose[b] | Median total dose (range) (μmol/kg) |
|---|---|---|---|---|
| [structure: CNC-L-alanine-estradiol-3,17-diester] | CNC—L-alanine-estradiol-3,17-diester | VI  a**  b**  c** | 54  75  105 | 212 (212–212)  300 (300–300)  420 (315–420) |
| [structure: CNC-L-alanine + estradiol] | CNC—L-alanine + estradiol | VII  a**  b* | 54 each  75 each | 212 (212–212)  300 (225–300) |
| [structure: CNC-L-alanyl-L-alanine-estradiol-3-ester] | CNC—L-alanyl-L-alanine-estradiol-3-ester | VIII  a*  b*  c* | 75  105  147 | 300 (75–300)  420 (210–420)  588 (294–588) |
| [structure: CNC-L-alanyl-L-alanine + estradiol] | CNC—L-alanyl-L-alanine + estradiol | IX  * | 75 each | 300 (150–300) |
|  | Ovariectomy | X  *  a*  b**  c*** | — | — |
|  | Untreated controls | XI | — | — |

[a] numbers of animals in groups I–X: 10 per subgroup in group XI: 20 per subgroup
[b] drugs were given at days 1, 8, 22 and 29 after randomization
*experiment 1;
**experiment 2;
***experiment 3

TABLE 2

Treatment of MNU-induced rat mammary carcinoma with N—(2-chloroethyl)-N—nitrosocarbamoyl (CNC)-L-alanine and CNC-L-alanyl-L-alanine-linked to estradiol in comparison with unlinked single agents and ovariectomy.
Efficacy of treatment

| Group No. | | Median tumor number per animal (95% confidence limits) | | | Median tumor volume per animal (cm$^3$) (95% confidence limits) | | | T/C × 100[a] | |
|---|---|---|---|---|---|---|---|---|---|
| | | week 1 | week 4 | week 7 | week 1 | week 4 | week 7 | week 4 | week 7 |
| I | a | 3.5 (1–5) | 8 (7–10) | 8 (2–11) | 1.2 (0.8–2.8) | 12.8 (3.9–22.8) | 18.1(2.7–29.2) | 62 | 63 |
| | | 2.5 (1–6) | 5 (1–11) | 6 (3–12) | 1.4 (0.9–4.5) | 5.8 (1.7–18.1) | 11.4 (1.1–19.3) | 38 | 39 |
| | | 3.5 (3–6) | 8 (0–8) | 6 (3–8) | 1.0 (0.9–1.7) | 8.5 (2.0–10.5) | 13.5 (3.6–23.5) | 32 | 50 |
| II | a | 4 (2–6) | 7 (6–9) | 8 (6–11) | 0.9 (0.7–1.1) | 24.9 (11.3–42.8) | 21.8 (20.4–33.7) | 90 | 71 |
| | b | 5 (2–6) | 10 (7–12) | 9.5 (5–12) | 1.0 (0.8–1.8) | 12.7 (8.1–23.6) | 17.9 (10.9–32.2) | 62 | 58 |
| | c | 4 (3–5) | 6 (3–7) | 5 (1–10) | 0.9 (0.7–1.5) | 7.3 (0.3–15.0) | 20.1 (0.5–43.1) | 25 | 60 |
| III | a | 4.5 (3–6) | 6 (4–8) | 5 (2–9) | 1.1 (0.7–4.4) | 8.2 (4.4–16.6) | 13.8 (5.1–15.6) | 48 | 44 |
| | b | 4 (1–4) | 3 (1–6) | 5 (1–7) | 1.2 (0.8–1.5) | 2.1 (0.5–10.3) | 4.1 (0.4–27.2) | 21 | 35 |
| | c | 3 (1–4) | 3 (1–4) | 2 (1–3) | 1.0 (0.7–1.6) | 2.9 (0.2–5.3) | 6.5 (0.5–11.5) | 15 | 23 |
| IV | a | 3 (2–5) | 8 (7–9) | 10 (9–11) | 0.8 (0.7–1.8) | 19.6 (14.7–24.6) | 36.6 (11.8–59.9) | 72 | 107 |
| | b | 3 (2–6) | 8.5 (4–11) | 8.5 (8–9) | 0.9 (0.8–1.3) | 23.2 (5.8–70.7) | 31.7 (26.5–36.8) | 96 | 94 |
| V | a | 3 (1–5) | 3.5 (3–5) | 4 (2–8) | 1.0 (0.7–1.1) | 3.9 (1.7–6.7) | 15.0 (6.7–33.2) | 19 | 51 |
| | b | 2.5 (2–5) | 2.5 (2–4) | 2 (1–4) | 0.9 (0.7–1.2) | 1.7 (0.2–3.0) | 3.31 (1.0–8.9) | 9 | 12 |
| | c | 2.5 (2–4) | 4 (2–6) | 3 (1–7) | 1.2 (0.9–2.5) | 1.8 (0.8–8.2) | 2.2 (0.4–5.7) | 18 | 10 |
| | d | 5.5 (1–8) | 5.5 (3–8) | 6 (2–6) | 1.3 (1.0–2.6) | 3.9 (1.0–6.7) | 6.3 (2.0–12.6) | 19 | 26 |
| | e | 5 (3–6) | 5 (3–8) | 5 (3–9) | 1.5 (0.7–2.4) | 3.7 (1.5–11.6) | 7.7 (3.4–21.9) | 25 | 34 |
| | f | 4.5 (1–6) | 4.5 (1–10) | 3 (2–4) | 1.1 (0.8–1.7) | 1.6 (0.7–5.8) | 5.2 (2.4–7.9) | 10 | 19 |
| VI | a | 4 (3–5) | 4 (1–5) | 5.5 (3–12) | 1.0 (0.8–1.5) | 8.2 (2.6–15.2) | 23.0 (7.6–57.5) | 38 | 97 |
| | b | 2 (1–5) | 5 (3–7) | 6 (3–8) | 1.0 (0.8–2.1) | 5.1 (0.9–13.4) | 1.3 (0.4–23.1) | 28 | 48 |
| | c | 2.5 (1–5) | 2 (2–5) | 3 (1–7) | 1.2 (0.8–2.9) | 3.6 (0.8–6.9) | 10.8 (0.3–16.8) | 16 | 29 |
| VII | a | 3 (2–4) | 4 (3–7) | 4 (3–7) | 1.0 (0.7–1.1) | 4.1 (2.6–9.2) | 8.5 (6.0–10.9) | 25 | 32 |
| | b | 4 (3–5) | 6 (4–6) | 6 (5–8) | 1.2 (0.7–2.1) | 5.2 (1.7–17.21) | 4.5 (3.9–10.7) | 42 | 24 |
| VIII | a | 4 (3–5) | 4 (3–7) | 4 (2–6) | 1.1 (0.8–1.9) | 5.1 (2.3–12.9) | 6.3 (0.7–11.8) | 35 | 25 |
| | b | 3 (1–6) | 4 (2–6) | 3 (2–4) | 1.1 (0.8–1.7) | 3.1 (1.7–5.8) | 6.1 (3.1–9) | 18 | 23 |
| | c | 3 (2–5) | 4 (2–5) | 4 (3–5) | 1.3 (1.1–1.7) | 1.4 (0.3–8.3) | 3.2 (1.8–5.2) | 18 | 13 |
| IX | | 4.5 (1–7) | 5 (3–7) | 3 (3–8) | 1.3 (0.8–1.6) | 3.6 (1.1–10.1) | 3.4 (0.8–8.8) | 32 | 16 |
| X | | 4 (3–5) | 3 (2–5) | 4 (3–6) | 1.3 (1.0–1.5) | 2.0 (0.5–4.9) | 12.4 (4.0–33.3) | 12 | 69 |
| XI | a | 4.5 (2–6) | 7.5 (6–9) | 7 (6–8) | 1.0 (0.8–1.7) | 19.5 (13.6–25.0) | 22.8 (17.6–29.2) | 100 | 100 |
| | b | 3 (2–4) | 7 (6–9) | 7 (6–9) | 1.0 (0.8–1.5) | 23.0 (15.0–30.6) | 27.9 (19.7–39.1) | 100 | 100 |
| | c | 4 (2–5) | 9 (7–11) | 10 (7–12) | 0.9 (0.7–1.1) | 23.1 (19.6–36.5) | 37.2 (20.6–43.3) | 100 | 100 |

[a] mean tumor volume of treated rats in % of untreated control

TABLE 3

Treatment of MNU-induced rat mammary carcinoma with N—(2-chloroethyl)-N—nitroscarbamoyl (CNC)-L-alanine- and CNC-L-alanyl-L-alanine-linked to estradiol in comparison with unlinked single agents and ovariectomy.

| Treatment group | | % Mortality | | | Median weight of animals (95% confidence limits (g) | | | Median survival time (days) (95% confidence limits) | ILS[a] |
|---|---|---|---|---|---|---|---|---|---|
| | | week 4 | week 7 | week 10 | week 1 | week 7 | % difference | | |
| II | a | 0 | 20 | 50 | 240 (215–260) | 260 (195–285) | +8 | 64.5 (43–93) | −5 |
| | b | 20 | 30 | 70 | 243 (235–260) | 230 (195–270) | −5 | 50.5 (15–98) | −26 |
| | c | 70 | 70 | 90 | 235 (210–260) | 250 (200–255) | +6 | 13.0 (7–46) | −81 |
| II | a | 0 | 10 | 30 | 235 (210–255) | 238 (205–270) | +1 | 82.0 (45–97) | +39 |
| | b | 10 | 20 | 40 | 240 (230–270) | 248 (200–305) | +3 | 69.0 (41–81) | +17 |
| | c | 20 | 20 | 70 | 228 (200–245) | 233 (200–245) | +2 | 60.0 (23–88) | +2 |
| III | a | 10 | 50 | 90 | 250 (240–270) | 210 (195–235) | −16 | 49.0 (28–62) | −28 |
| | b | 30 | 50 | 90 | 248 (210–255) | 270 (195–240) | −15 | 38.0 (10–63) | −44 |
| | c | 40 | 70 | 100 | 238 (205–255) | 170 (165–185) | −29 | 24.5 (10–50) | −64 |
| IV | a | 0 | 60 | 90 | 238 (190–260) | 218 (200–245) | −8 | 40.0 (33–79) | −32 |
| | b | 30 | 80 | 90 | 230 (205–260) | 215 (195–235) | −7 | 33.0 (21–48) | −44 |
| V | a | 0 | 30 | 70 | 228 (220–260) | 235 (195–260) | +3 | 53.0 (44–86) | −30 |
| | b | 0 | 20 | 30 | 245 (210–255) | 228 (210–265) | −7 | 65.0 (41–94) | −14 |
| | c | 0 | 30 | 30 | 240 (220–260) | 230 (180–265) | −4 | 80.0 (40–88) | +18 |
| | d | 0 | 10 | 70 | 240 (220–250) | 190 (170–230) | −21 | 50.0 (43–65) | −26 |
| | e | 0 | 50 | 90 | 235 (225–260) | 210 (170–235) | −11 | 43.0 (36–57) | −37 |
| | f | 20 | 80 | 90 | 248 (225–260) | 233 (220–245) | −6 | 34.5 (16–56) | −49 |
| VI | a | 0 | 20 | 90 | 235 (225–250) | 230 (195–245) | −2 | 50.0 (39–63) | −34 |
| | b | 0 | 20 | 80 | 242 (220–280) | 217 (180–260) | −10 | 54.0 (39–68) | −29 |
| | c | 0 | 50 | 100 | 247 (215–260) | 200 (150–230) | −19 | 45.0 (32–54) | −41 |
| VII | a | 0 | 10 | 20 | 230 (215–250) | 220 (200–250) | −4 | 99.0 (59–114) | +30.3 |
| | b | 0 | 70 | 90 | 238 (215–280) | 230 (175–250) | −3 | 35.0 (28–64) | −49 |
| VIII | a | 10 | 40 | 60 | 245 (230–265) | 230 (170–255) | −6 | 52.0 (25–109) | −24 |
| | b | 10 | 80 | 100 | 235 (225–255) | 215 (185–245) | −9 | 33.5 (26–53) | −51 |
| | c | 10 | 70 | 90 | 238 (225–250) | 230 (225–240) | −3 | 35.5 (25–57) | −48 |
| IX | | 10 | 30 | 70 | 238 (230–250) | 205 (190–290) | −14 | 59.0 (26–73) | −13 |
| X | | 0 | 10 | 30 | 245 (235–270) | 315 (305–350) | +29 | 104 (72–127) | +53 |
| XI | a | 0 | 10 | 50 | 240 (235–254) | 275 (250–295) | +15 | 68.0 (51–90) | — |
| | b | 0 | 20 | 55 | 230 (225–240) | 265 (240–290) | +15 | 76.0 (52–90) | — |
| | c | 5 | 21 | 58 | 230 (215–240) | 245 (205–250) | +7 | 59.0 (44–86) | — |

[a] Increase in median life span

TABLE 4

Chemotherapeutic efficacy of CNC-L-alanine-estradiol-17-ester on MNO-induced mammary carcinoma of SD-rats, that have been ovariectomized before manifestion of tumors.

| Group No. | Median tumor number per animal (95% confidence limits) | Median tumor volume per animal (cm³) (95% confidence limits) | T/C × 100 | Median weight of animals (g) (95% confidence limits) | Mortality N (%) |
|---|---|---|---|---|---|
| I[a] | 2 (1–2)[d] | 1.2 (0.9–3.4)[d] | — | 293 (260–300)[d] | 1 (0)[e] |
|  | 3 (2–4)[e] | 13.9 (3.9–28.2)[e] | 100[e] | 305 (290–335)[e] | 4 (29)[f] |
|  | 3 (2–5)[f] | 20.5 (6.0–52.3)[f] | 100[f] | 310 (290–335)[f] | 7 (50)[g] |
| II[b] | 1 (1–2)[d] | 0.8 (0.7–1.2)[d] | — | 275 (235–285)[d] | 2 (15)[e] |
|  | 3 (2–4)[e] | 3.3 (2.5–11.5)[e] | 24[e] | 245 (190–280)[e] | 7 (54)[f] |
|  | 3 (1–5)[f] | 6.5 (1.8–59.2)[f] | 32[f] | 218 (195–270)[f] | 11 (85)[g] |
| III[c] | 2 (1–2)[d] | 0.8 (0.7–1.0)[d] | — | 265 (235–310)[d] | 5 (38)[e] |
|  | 2 (1–4)[e] | 3.3 (1.5–41.4)[e] | 24[e] | 230 (200–285)[e] | 7 (54)[f] |
|  | 2 (1–5)[f] | 5.9 (2.9–10.5)[f] | 29[f] | 238 (205–295)[f] | 7 (54)[g] |

[a]untreated control, N = 14 animals
[b]treatment with 75 μmol/kg CNC-L-alanine-estradiol-17-ester on days 1, 8, 22 and 29 after randomization, N = 13 animals
[c]treatment with 75 μmol/kg CNC-L-alanine on days 1, 8, 22 and 29 after randomization, N = 13 animals
[d]week 1
[e]week 4
[f]week 7
[g]week 10

The foregoing description of specific embodiments will so fully reveal the general nature of the invention that others can, by applying current knowledge, readily modify and/or adapt such specific embodiments without departing from the generic concept, and therefore such adaptations and modifications should and are intended to be comprehended within the meaning and range of equivalents of the disclosed embodiments. It is to be understood that the phraseology or terminology employed herein is for purpose of description and not of limitation.

What is claimed is:

1. Steroid-N-2-halogenethyl-N-nitroso-carbamoyl amino acid esters selected from the group consisting of N-(2-chloroethyl)-N-nitroso carbamoyl-L-alanyl-L-alanine-estradiol-17-ester; N-(2-chloroethyl)-N-nitrosocarbamoyl-L-alanyl-estradiol-17-ester; and N-(2-chloroethyl)-N-nitrosocarbamoyl-L-alanine-estradiol-3,17-diester.

* * * * *